United States Patent [19]

Thome

[11] Patent Number: 4,506,549

[45] Date of Patent: Mar. 26, 1985

[54] METHOD AND DEVICE FOR THE AUTOMATIC CHECKING OF THE SOUNDNESS OF THE WELDS OF MECHANO-WELD ASSEMBLIES

[76] Inventor: Paul Thome, 8 rue Coutureau, Saint Cloud, France, 92210

[21] Appl. No.: 327,033

[22] Filed: Dec. 3, 1981

[30] Foreign Application Priority Data

Dec. 9, 1980 [FR] France .................. 80 26071

[51] Int. Cl.³ .................................................. G01N 29/04
[52] U.S. Cl. ................................ 73/582; 73/622; 73/623
[58] Field of Search ............... 73/582, 588, 622, 623, 73/637, 638, 640

[56] References Cited

U.S. PATENT DOCUMENTS

| | | | |
|---|---|---|---|
| 3,002,375 | 10/1961 | Moffatt et al. ................... | 73/640 |
| 3,809,607 | 5/1974 | Murray et al. .................... | 73/623 |
| 3,862,578 | 1/1975 | Schlüter ............................ | 73/623 |
| 4,155,243 | 5/1979 | Elsner .............................. | 73/623 |
| 4,218,923 | 8/1980 | Triplett et al. ................... | 73/623 |

Primary Examiner—Anthony V. Ciarlante
Attorney, Agent, or Firm—Holman & Stern

[57] ABSTRACT

The invention relates to a device for the automatic checking of welds between tubular parts. A carriage comprises two fixed ends with their centering wheels, a movable mechanism with two flanges and guide rails. This mechanism rotates on bearings. The carriage includes a drum moving over rails and bearing a telescopic arm orientable by rotation on its axis. The end of the arm carries an inspection head. Digital control ensures the programming of the movement and the orientation of the inspection head opposite the weld. The device and method are useful for the ultrasonic checking of the welds of the nodes of offshore platforms and for the checking of welds in nuclear power systems.

6 Claims, 9 Drawing Figures

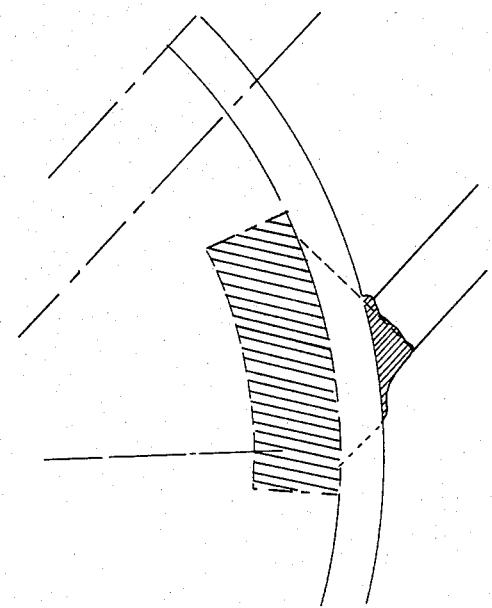
FIG. IA
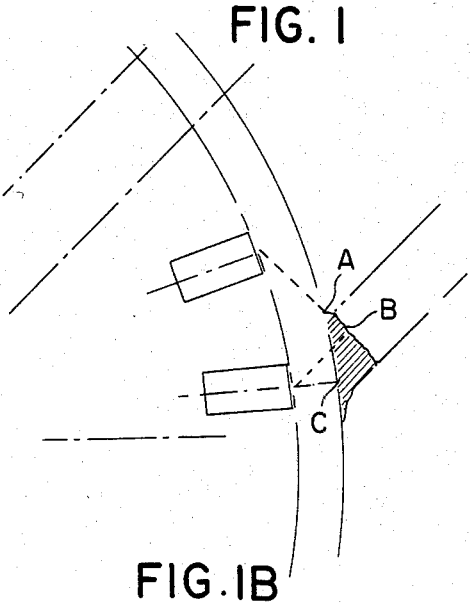
FIG. IB
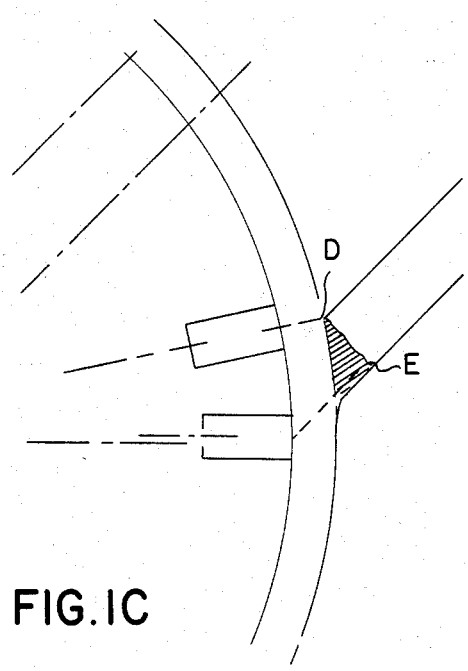
FIG. IC
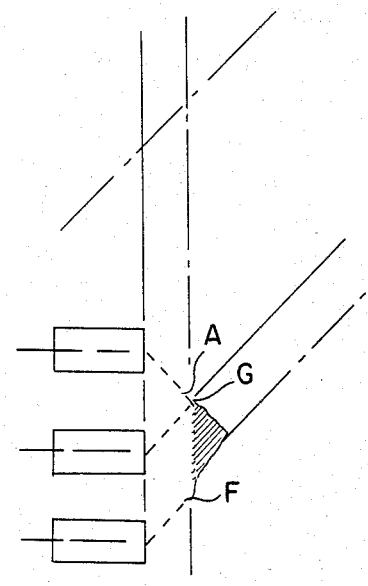
FIG. ID

METHOD AND DEVICE FOR THE AUTOMATIC CHECKING OF THE SOUNDNESS OF THE WELDS OF MECHANO-WELD ASSEMBLIES

BACKGROUND OF THE INVENTION

Field of the Invention

The present invention relates to a method and a device for automatic checking designed to detect, to measure, to watch possible cracks and other damage in mechano-weld assemblies, non-destructively.

The invention relates more particularly to a vehicle moving inside a hollow body, bearing a robot arm serving to position measuring probes in contact with areas to be checked.

Whether it relates to complying with the requirements of quality in manufacture (initial control) or monitoring changes during use (possible damage, corrosion, fatigue . . . ), it is in a good many cases necessary and required by regulations to ensure the soundness of a structure and to give warning of the risk of accident. These diagnoses have already been imposed on nuclear power stations, for example, and they will soon be likewise required more critically on off-shore platforms.

At present and even for the aforementioned example, in a good many cases testing is carried out manually, which considerably limits the confidence which can be expected of these measurements (off-shore) or requires an appreciable time and involves the absorption of radiation for the operators (nuclear power stations).

In its nature, the method used here measures the parameters defining a defect: location, orientation, dimensions. It is compatible with memorization of all the corresponding values; in addition, being automatic it overcomes uncertainties which accompany any manual method.

It is particularly intended for the inspection of tubular assembly welds where one of the elements is accessible from the inside. It responds to difficult environmental conditions, whether it relates to a confined space or a hostile environment such as that in nuclear power stations or off-shore. It is suitable for checking tubular assemblies whether it relates to the joining up of pipes, cappings, or again tubular trellis works with their fastening nodes between the principal members (barrels or piers, cords) and secondary members (bracings).

In the case, for example, of off-shore platforms, which attain huge sizes, welds are counted in hundreds. The trellis-work nodes include up to 6 to 8 bracings with or without stiffening gussets. These welds coincide with particularly stressed zones liable through their complex nature to be subjected to manufacturing defects, and through their situation subject to alternating stresses which can generate fatigue cracks.

It is an object of the invention to provide a method enabling direct, exhaustive, precise and rapid reproducible measurements of such welded joints and which do not require the intervention on site of an operator.

It is another object of the invention to provide a method which responds to the exigencies of surveillance in service ("in-service inspection").

It is another object of the invention to provide a device for performing the last-mentioned methods by positioning positively and orienting correctly the measuring sensors within some millimeters with respect to the weld beads and to explore under these conditions the integrity of the weld bead (scanning of the weld by sensors).

GENERAL DESCRIPTION OF THE INVENTION

According to the invention there is provided a method for the automatic non-destructive checking of welds between two members where the inspection head is at any moment oriented to remain in the same configuration with respect to the direction of the weld bead, characterised in that the checking is carried out through the inner surface of the principal member and that the position of the measuring head is servo-coupled to that of the weld bead.

According to a preferred embodiment of the method according to the invention the position of the weld head is detected from a measurement along a generatrix and a measurement along a circular cross-section, the inspection device then being adjusted in position from these two measurements, and the movement of the inspection head being programmed by digital control.

According to another aspect of the invention there is provided a checking device for the application of the last-mentioned method constituted by a carriage movable inside the member, carrying a radial telescopic arm with, at its end, an inspection head endowed with four degrees of freedom (along the axis of the carriage, radially, in rotation around the axis of the carriage, and in rotation on itself).

According to another feature of the invention there is provided a carriage suitabe for use in the last-mentioned device comprising two fixed ends bearing centering wheels for the carriage in the member and a system of locking against the latter, two flanges connected by guide rails forming a mechanism rotatable on itself between the two fixed ends, a drum which is moved on guide rails and which bears a telescopic radial arm rotating on itself, possessing on its end the inspection head.

In devices of this type, feelers or sensors are provided which emit signals and receive echos or "images" which manifest the presence of defects. Preferably, eddy current probes or ultrasonic probes are used. The measuring head is moved against the inner surface of the member, opposite the weld.

Other features and advantages will become apparent from the detailed description which follows given in conjunction with the accompanying drawings.

BRIEF DESCRIPTION OF THE DRAWINGS

FIGS. 1a to 1d show the scanning zone of feelers or sensors in a checking device according to the invention in cross-sectional diagrammatic view.

FIG. 4a shows a view in horizontal section of the internal scanner along the line III—III in the embodiment shown in FIG. 2.

FIG. 4b shows a vertical section along the line IV—IV' of the internal scanner embodiment shown in FIG. 4a.

DESCRIPTION OF A PREFERRED EMBODIMENT

Figure 2:
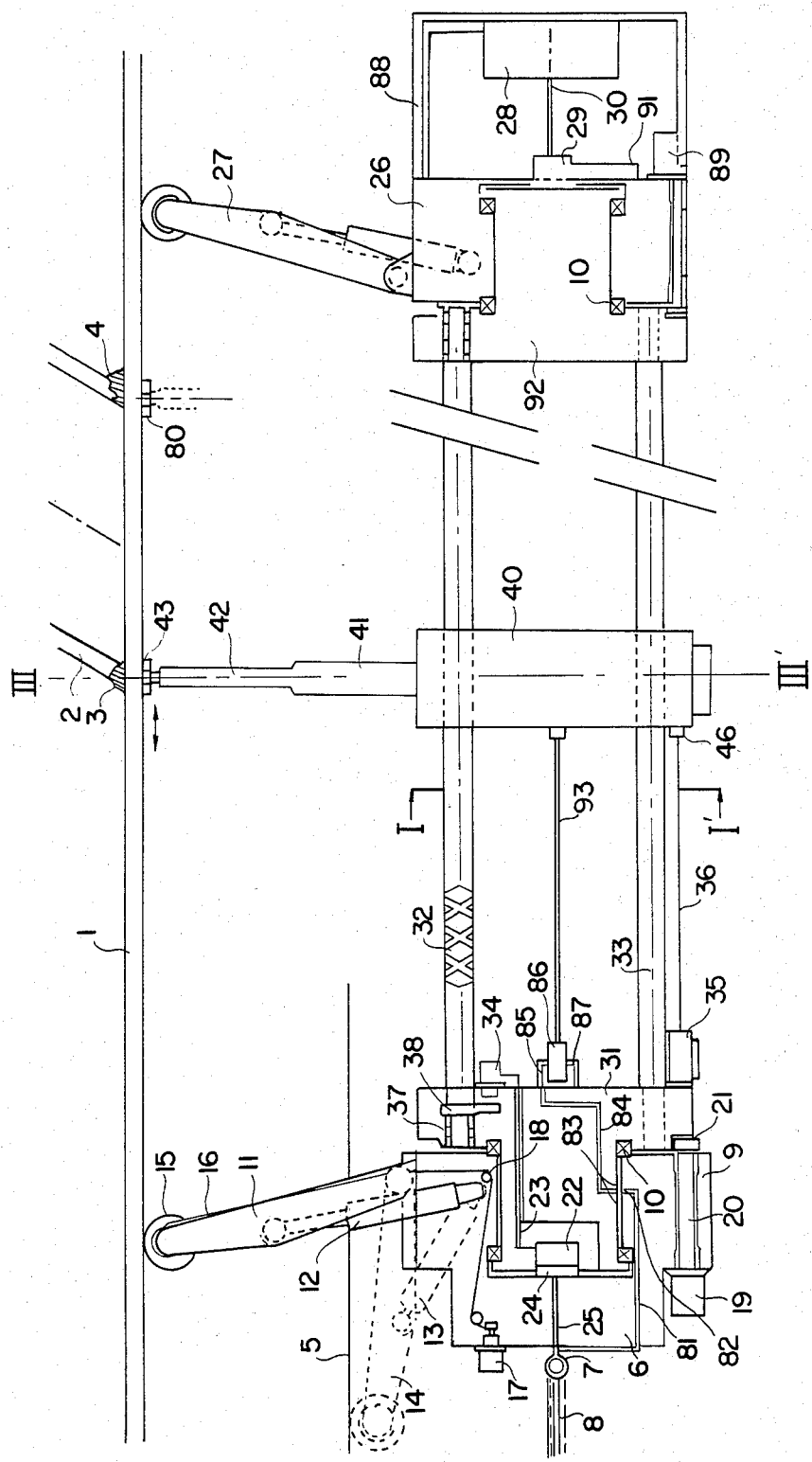
FIG. 2 shows in longitudinal diagrammatic section a checking device lowered into a vertical member on which secondary members are fastened by fully penetrating welds.

In the embodiment shown in the drawings, the scanning zone of the sensors is indicated in FIG. 1a. Cracks are detected by ultrasonic perpendicular and angular detectors. The width of the weld corresponds to the zone of disappearance of echos of waves from the perpendicular sensors, on the outer surface; thus the irregularities of recording reveal lack of penetration at the weld root (defect "D" in FIG. 1).

Other cracks, adhesions and inclusions (A,B,C,-D,E,F,G FIG. 1) are detected in the emittor-receiver ("pulse-echo") mode. It is seen in these FIGS. 1 that there is no difficulty in detecting cracks on the principal member, and that, inasmuch as the welds may are fully penetrated, all cracks in the weld and in the secondary member will also be detected.

The checking device which is moved inside a member enables checking of the welds of secondary members when these welds are fully penetrated.

It has the function of moving a probe against or close to the inner surface of the member, of recognizing the position of the welds and of effecting the exploration thereof to find possible cracks, by scanning this weld with waves correctly oriented with respect to the direction of the weld.

Figure 3:
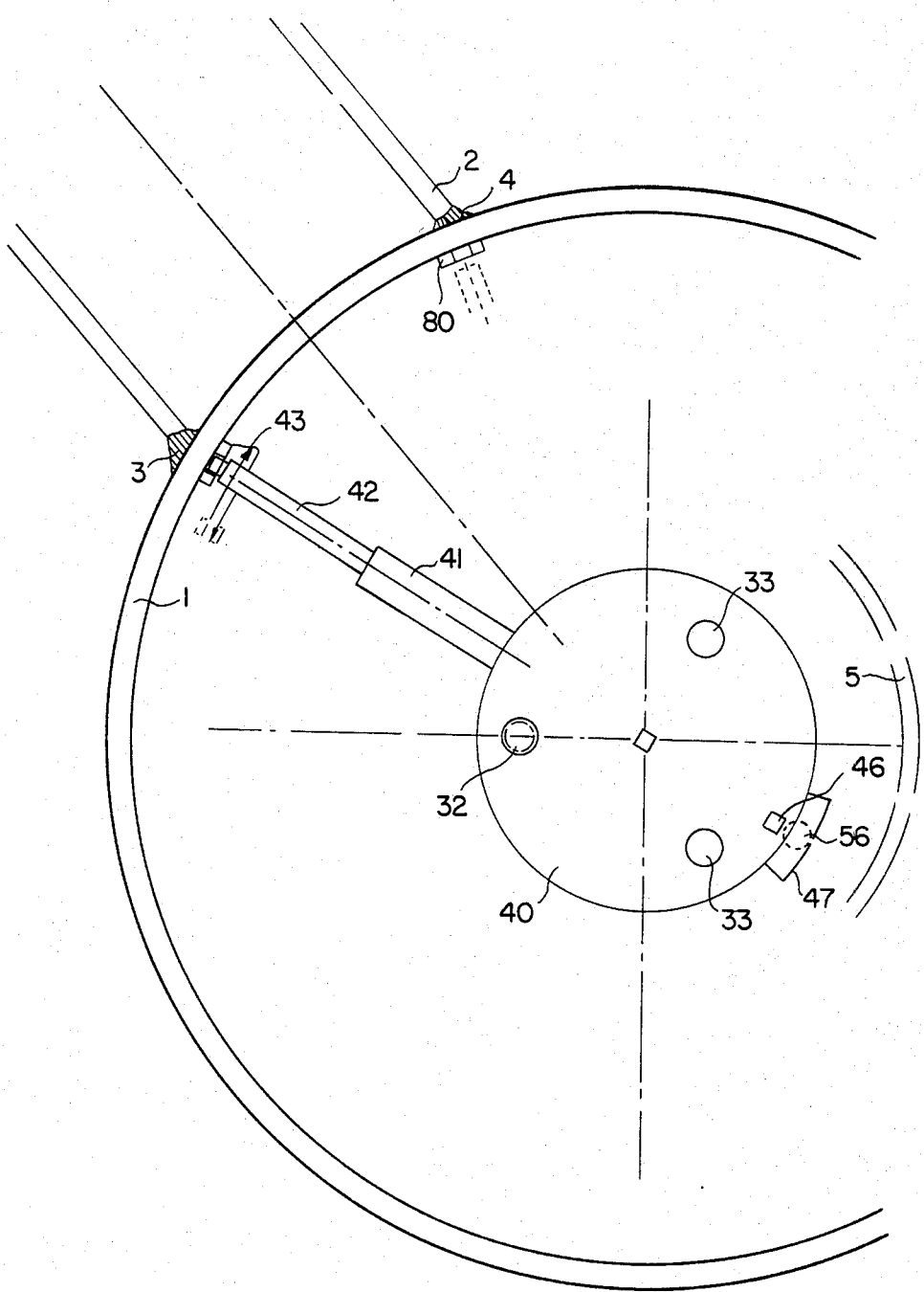
FIG. 3 shows a horizontal cross-section through the line I—I' of FIG. 2.
Figures 4A, 4B:
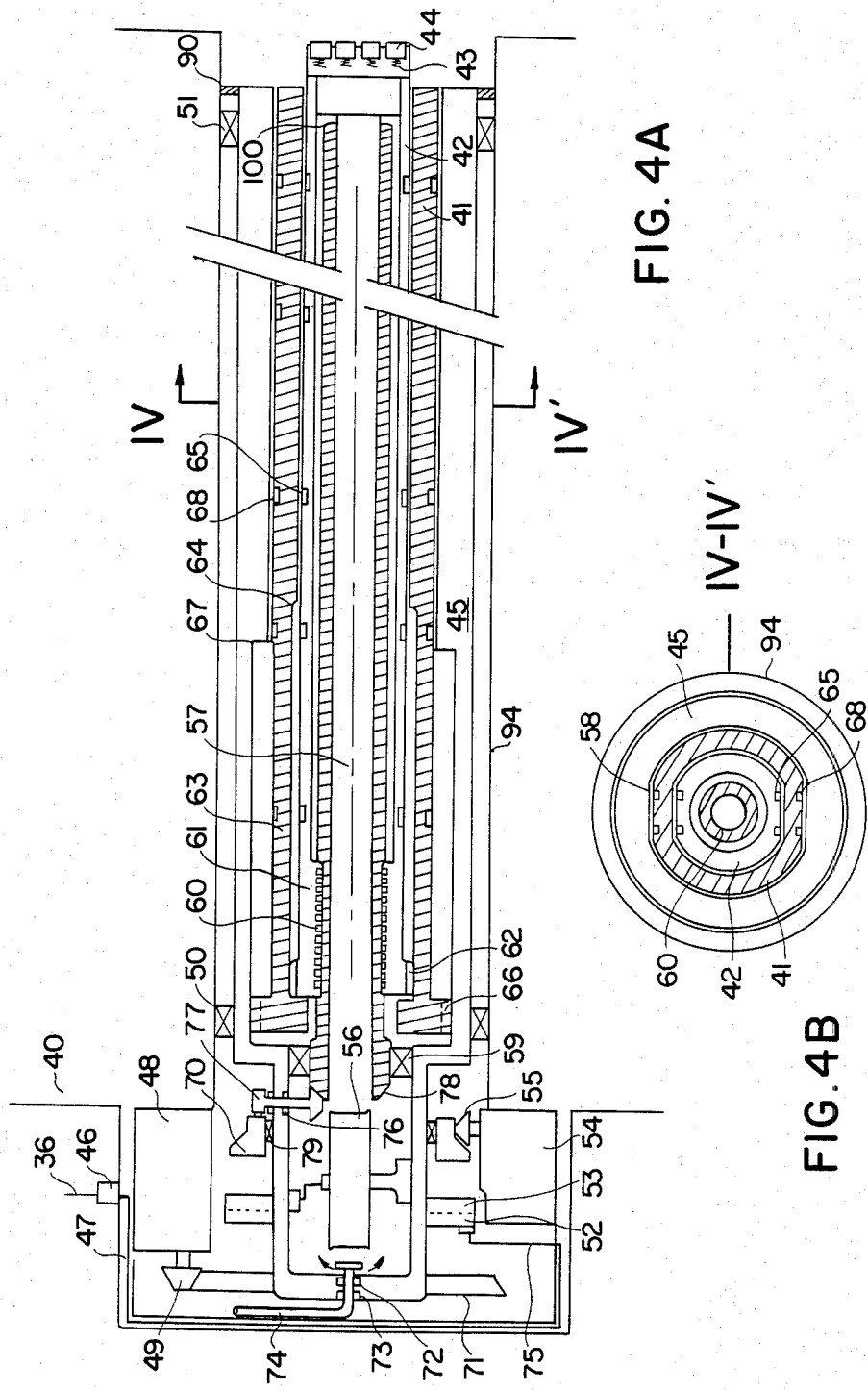
Figure 5:
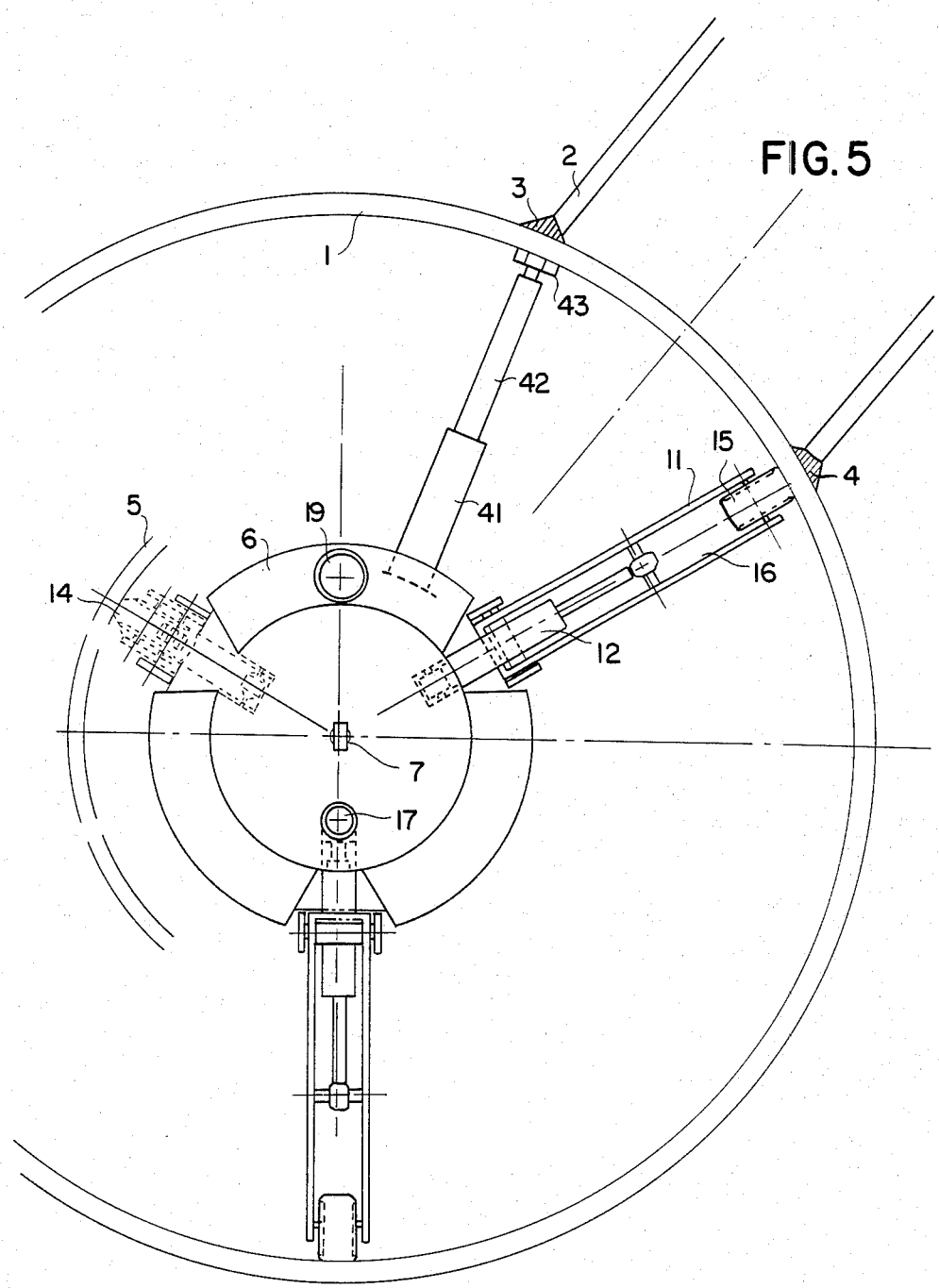
FIG. 5 shows in more detail the device of FIG. 2 viewed longitudinally through the member being checked.

In the example illustrated in FIGS. 2, 3, 4, 5, this "internal scanner" (SCI) is lowered into a vertical member 1 on which secondary members 2 have been fastened by fully penetrating welds 3. These welds are checked by an assembly of ultrasonic sensors 44 constituting the measuring probe 43. When the probe checks the diametrally opposite position of the weld, at 4, this probe has come to 80 and it has rotated by 180° on itself. The SCI ("internal scanner") is supported by cables 8 connected to a crank-pin 7. These cables ensure the mechanical support, and electrical supply of the motors, the instrumentation and a demineralized water circuit ensuring the coupling of the probe. If the members were horizontal, a self-driven carriage would be integrated with the SCI.

The SCI rolls and is centered inside 1 by means of arms 11 and 27 provided with wheels 15 at their end. These arms are deployed by jacks 12. These arms adjust themselves through a range of diameters of the member. The minimum diameter is shown by the member 5 to which corresponds the position 13 and 14 of the jack 12 and of the arm 11 respectively. When the SCI is in a selected position, defined to within some 10 centimeters, the wheels 14 are locked by braking through cables 16 which, through return pulleys 18, are actuated by a motor 17.

The SCI includes a fixed part 6 with respect to cables 8, a movable part in squirrel cage form rotating around the axis of the SCI, and a lower part also fixed. On the rotary part the module 40 bearing the probe 43 is moved. The telescopic sensor-holder 41, 42 is extended to become urged against the inner surface and is capable of being oriented by rotation around its axis.

The upper fixed part includes a ring 9 as well as the lower fixed part 26. On this ring are placed bearings and ball-bearings stops 10 positioning the movable part. Through the upper fixed part pass electrical supply cables 25 and the supply cables connected to the probe. These cables extend to a multi-polar sliding electrical collector, having a fixed part 24 and a rotary part 22, the latter being integral in rotation with the movable part.

The electrical cables 23 supply the steppping electrical motor 34 which ensures the movement of the module 40. On the upper fixed part is fixed the stepping motor 19 which, through the axle 20 and the pinion 21 ensures the rotation of the movable part 31. The fixed ring 9 is also provided with a demineralized water supply arriving through the pipe 81 and opening into a cylindrical groove 82. This water circuit serves to supply the movable part through a pipe 84 opening into the chamber bounded between the fixed part and the movable part by toric fluid-tight seals 83.

The lower fixed part 26 includes a stepping motor 89 coupled with the motor 19. The collector 29 ensures electrical connection with the lower rotary part 92. An electrohydraulic unit 28 supplied by 30 actuates the jacks of the arms 27. This unit is protected by a cover 88.

The rotary movable part comprises an upper cylindrical flange and a lower cylindrical flange connected by tie rods 33 and by a ball screw 32. The electrical supply of the lower fixed part is effected through cables passing within 33. The demineralized water circuit 84 is connected to a drum-winder 86 borne by the arm 87. From this drum leads the pipe 93 ensuring the water supply to the module 40. In the same way, a drum-winder 35 holds the electrical supply and instrumentation cables 36 connected to the module 40 under tension.

The module 40 is moved over the tie-rods 33. It is driven by the ball screw 32, held by the bearings 37, and whose rotation is actuated by the stepping motor 34 driving the gear ring 38. The module 40 has the function of ensuring the support of the sensors (of the probe) against the member and of orienting this probe with respect to the weld. The instrumentation cables are connected to the probes which, in addition, are immersed in a flow of demineralized water or any other coupling fluid.

These functions are carried out in the manner explained below.

The module includes a radial, cylindrical shaft 94. This shaft contains a jacket 45 centered by bearings 50 and 51 and whose rotation relative to 40 is controlled by a stepping motor 48 driving through a conical pinion 49 a toothed ring 71 fast to 45. The end of 45 includes an annular electrical collector of which one surface 53 is fast to 45 whilst the other surface 52 is fast to the module. The collector is connected by the cables 75 to the connecting plug 46 which receives the end of the cable 36.

A sealing ring 90 protects the chamber comprised between 94 and 45.

At the end and inside 45 is fixed the winder-drum 56 ensuring the maintenance of the instrumentation cable 57 connected to the probe under tension. A water pipe 74 fast to 40 passes coaxially through the surface of the jacket 45. It is centered by a bearing 73 and possesses a fluid-tight toric seal 72. This end is protected by the fixed cover 47. This end is also traversed radially by an axle bearing two pinions; the upper cylindrical pinion is driven by a ring 70 centered by the bearing 79. The inner conical pinion drives the end 78 of the threaded axle 60 whose rotation will ensure the deployment of the telescopic arm. The rotation of the ring 70 is controlled by the stepping motor 54 with its conical pinion 55 driving the corresponding conical teeth of 70. The fluid tightness is ensured by the seal 76.

The telescopic arm includes an inner tube 42 and a coaxial tube 41. They slide without rotating inside 45 due to flats 58, and they are hence servo-coupled to the rotation of 45. The tube 41 includes self-lubricating guide bearings 66 and 68. The tube 42 includes self-lubricating guide bearings 62 and 65. The travel of the inner tube is defined by the length of the bearing 63 up to the stop 64. The travel of the outer tube 41 is limited at the stop 67 of the jacket.

The deployment of the telescopic tube is controlled by the rotation of the threaded axle 60 on which slides a nut 61 with return of balls fast to the inner tube 42. This axle is kept concentric by a bearing 59 urged against the jacket and by a teflon ring 100 at the other end.

The head of 42 carries the probe 43 equipped with ultrasonic sensors 44 mounted individually on springs so as to compensate for the curve of the member and thus ensure correct coupling.

The operation of the SCI is as follows: the SCI is lowered to within about ten centimeters from a marked position and it is blocked in position. The module is then moved rapidly once the probe has been extended and is brought into contact with the inner surface of the tube. The probe records the passage of the weld when it no longer receives the return echos from the outer surface of the member. It hence intercepts in its path two signals corresponding to crossing the weld by the same generatrix.

The module is then positioned at a half-distance between these signals and then a rotation is imparted to it. The new signals in this direction transverse to the first, define the axis of the secondary member. Since the dimensions and inclinations of the node are known, the theoretical profile of the weld is known. Since the center of this weld is known, then its position on the member is known with satisfactory precision. The stepping motors are then actuated in order that the probe may scan the weld completely and remain constantly oriented perpendicularly to the tangent of the weld. In fact the ultrasonic transducers emit transverse waves (inclined to the normal of the surface) which must be correctly oriented to detect the cracks along the weld bead. Possibly the weld also sweeps the bead transversely by moving gradually along the latter. All these operations are carried out by digital control.

I claim:

1. A device for the automatic, non-destructive test scanning of welds between two members, at least one of which is hollow, comprising a carriage movable inside the hollow member, a radial telescopic arm borne on said carriage with, at its end, an inspection head with sensors and having four degrees of freedom: (i) along an axis of the carriage, (ii) radially, (iii) in rotation around the axis of the carriage, and (iv) in rotation on itself; the carriage comprising two fixed ends, bearing wheels for centering the carriage in the hollow member and a system of locking the carriage against the hollow member, which system has two flanges connected by guide rails forming a mechanism rotatable on itself between the two fixed ends, and a drum which is moved on guide rails and which bears a telescopic radial arm capable of rotating on itself, having the inspection head at its end.

2. The device of claim 1 wherein the inspection head is traversed by a flow of water ensuring the coupling of the sensors and protecting mechanism against any pollution, and wherein electrical connections and supplies of fluids are ensured by cylindrical or annular collectors forming a connection between the fixed ends and movable flanges.

3. The device of claim 2 wherein extension and orientation movements of the telescopic arm of the drum are effected by motors in a fluidtight space, wherein the bodies of the arms include on the outside an annular electrical collector and on the inside a winder receiving instrumentation cables.

4. The device of claim 1 wherein said sensors are adapted to scan the weld by eddy current detectors.

5. The device of claim 1 wherein said sensors are adapted to scan the weld by ultrasonic detectors.

6. The device of claim 5 wherein said detectors are straight and angled ultrasonic detectors.

* * * * *